United States Patent
Hwang et al.

(10) Patent No.: US 11,597,709 B2
(45) Date of Patent: Mar. 7, 2023

(54) PREPARING METHOD FOR 5-ALKOXYMETHYLFURFURAL

(71) Applicant: KOREA RESEARCH INSTITUTE OF CHEMICAL TECHNOLOGY, Daejeon (KR)

(72) Inventors: Dong Won Hwang, Daejeon (KR); Young Kyu Hwang, Daejeon (KR); Ma Eum Lee, Daejeon (KR); Pravin Pandharinath Upare, Daejeon (KR); Do Young Hong, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 125 days.

(21) Appl. No.: 17/167,886

(22) Filed: Feb. 4, 2021

(65) Prior Publication Data
US 2021/0253545 A1 Aug. 19, 2021

(30) Foreign Application Priority Data
Feb. 13, 2020 (KR) .................. 10-2020-0017437

(51) Int. Cl.
*C07D 307/50* (2006.01)
*B01J 31/02* (2006.01)

(52) U.S. Cl.
CPC ........ *C07D 307/50* (2013.01); *B01J 31/0205* (2013.01)

(58) Field of Classification Search
CPC ............................ C07D 307/50; B01J 31/0205
See application file for complete search history.

(56) References Cited

U.S. PATENT DOCUMENTS

| | | |
|---|---|---|
| 8,519,167 B2 | 8/2013 | Muñoz De Diego et al. |
| 9,090,579 B2 | 7/2015 | Binder et al. |
| 9,238,635 B2 | 1/2016 | Essayem et al. |
| 9,321,744 B1 | 4/2016 | Hsu et al. |
| 9,586,923 B2 | 3/2017 | Subramaniam et al. |
| 2010/0058650 A1 | 3/2010 | Gruter et al. |
| 2012/0059178 A1* | 3/2012 | Sanborn ............... C07D 307/68 549/485 |

(Continued)

FOREIGN PATENT DOCUMENTS

| | | |
|---|---|---|
| CN | 107501215 A | 12/2017 |
| JP | 2013-507358 A | 3/2013 |

(Continued)

OTHER PUBLICATIONS

Balakrishnan, Green Chemistry., 2012, 14, p. 1626-1634 (Year: 2012).*

(Continued)

*Primary Examiner* — Robert C Boyle
(74) *Attorney, Agent, or Firm* — Lewis Roca Rothgerber Christie LLP

(57) ABSTRACT

The present disclosure provides a preparing method for 5-alkoxymethylfurfural, including steps of (a) preparing fructose, (b) mixing the fructose, an organic acid catalyst, and an organic solvent, thereby preparing mixing solution, and (c) heating the mixing solution, thereby preparing 5-alkoxymethylfurfural.
Therefore, 5-alkoxymethylfurfural may be effectively prepared without by-products from fructose.

7 Claims, 2 Drawing Sheets

(56) References Cited

U.S. PATENT DOCUMENTS

| | | | |
|---|---|---|---|
| 2012/0283452 A1* | 11/2012 | Munoz De Diego | ..................... C07D 307/40 549/485 |
| 2014/0121389 A1 | 5/2014 | Essayem et al. | |
| 2015/0005516 A1 | 1/2015 | Binder et al. | |
| 2015/0183755 A1 | 7/2015 | Subramaniam et al. | |

FOREIGN PATENT DOCUMENTS

| | | |
|---|---|---|
| JP | 2014-515037 A | 6/2014 |
| JP | 2015-514699 A | 5/2015 |
| JP | 2018-016632 A | 2/2018 |
| KR | 10-2010-0061723 A | 6/2010 |
| KR | 10-2018-0090840 A | 8/2018 |
| WO | WO 2011/043660 A2 | 4/2011 |
| WO | WO 2013/043131 A1 | 3/2013 |

OTHER PUBLICATIONS

Amberlyst data sheet (Year: 2022).*
Li, Biomass and Bioenergy, 33 (2009) p. 1182-1187 (Year: 2009).*
Korean Office action for Application No. 10-2020-0017437, dated Jul. 26, 2021, 5 pages and machine translation, 6 pages.
Bing, Liu et al., "Efficient One-Pot Synthesis of 5-(Ethoxymethyl)furfural from Fructose Catalyzed by a Novel Solid Catalyst," Ind. Eng. Chem. Res., 2012, vol. 51, pp. 15331-15336.
Upare, et al., "An integrated process for the production of 2,5-dimethylfuran from fructose," Green Chemistry, 2015, 17, 3310-3313.
Rosatella, et al., "5-Hydroxymethylfurfural (HMF) as a building block platform: Biological properties, synthesis and synthetic applications," Green Chemistry, 2011, 13, 754-793.
Extended European Search Report for Application No. 21156173.3, dated Jul. 2, 2021, 9 pages.
Morales, G. et al., "Efficient production of 5-ethoxymethylfurfural from fructose by sulfonic mesostructured silica using DMSO as co-solvent," Catalysis Today 279 (2017) pp. 305-316.
Notice of Allowance for Korean Patent Application No. 10-2020-0017437, dated Dec. 23, 2021, 3 pages.
Japanese Office Action for Japanese Patent Application No. 2021-018025, dated Feb. 15, 2022, 9 pages.
Saravanamurugan, Shunmugavel, et al., "Conversion of Mono- and Disaccharides to Ethyl Levulinate and Ethyl Pyranoside with Sulfonic Acid-Functionalized Ionic Liquids," ChemSusChem 2011, 4(6), pp. 723-726.
Sun, Kai, et al., "Conversion of monosaccharides into levulinic acid/esters: Impacts of metal sulfates addition and the reaction medium," Journal of Chemical Technology and Biotechnology, 2019, V. 94, No. 11, pp. 3676-3686.
Bodachivskyi, Lurri, et al., "A systematic study of metal triflates in catalytic transformations of glucose in water and methanol: identifying the interplay of Bronsted and Lewis acidity," ChemSusChem 10.1002/cssc.201900292, 2019, 12(14), pp. 3263-3270.

* cited by examiner

PREPARING METHOD FOR 5-ALKOXYMETHYLFURFURAL

CROSS-REFERENCE TO RELATED APPLICATION

The present disclosure claims priority to and the benefit of Korean Patent Application No. 2020-0017437, filed on Feb. 13, 2020, the disclosure of which is incorporated herein by reference in its entirety.

BACKGROUND OF THE INVENTION

1. Field of the Invention

The present disclosure relates to a preparing method for 5-alkoxymethylfurfural, and more specifically, relates to a method for preparing 5-alkoxymethylfurfural from fructose.

2. Description of Related Art

Technologies for converting saccharides or a saccharide containing biomass to an economically useful compound have been continuously studied and developed. As one of them, fructose is monosaccharides having ketone as a reductor, is one of hexoses, widely exists in the vegetable kingdom, and is contained as a form of glass in fruits together with glucose or is combined with glucose, thereby existing as sucrose.

Recently, a technology of converting saccharides such as fructose to 5-hydroxymethylfurfural (hereinafter, referred to as "HMF") under an acid catalyst, and selecting it as a start material for obtaining a polyethylene terephthalate type bio-based monomer has been introduced.

HMF is a good start material for generating a furan monomer. However, there is a problem such that regardless of a mechanism for generating HMF from fructose, condensation, re-dehydration, an inverse reaction, and other rearrangements sequentially incur additional reactions in a reaction process, and due to the above, unwanted by-products occur.

Particularly, a process of preparing 2,5-furandicarboxylic acid from HMF is proceeded by preparing HMF through dehydration of fructose as a first step, and performing an oxidizing reaction of HMF as a second step.

In the case of performing dehydration of fructose in aqueous solution as the first step, generated HMF may be easily decomposed into levulinic acid and formic acid by a secondary reaction with water. Therefore, in order to enhance a yield rate of HMF, it is more preferable to use an organic solvent (e.g., 1-Butanol, GVL, DMF, etc.) having a high boiling point than the aqueous solution (refer to non-patent document 1. Green Chem., 2015, 17, 3310, and non-patent document 2. Green Chem., 2011, 13, 754).

In order to enhance a yield rate of 2,5-furandicarboxylic acid (hereinafter, referred to as "FDCA") in the oxidizing reaction of HMF, it is preferable to perform the reaction in the aqueous solution (refer to patent document 1. Korean publication of unexamined patent applications No. 10-2018-7018309).

Therefore, in order to prepare FDCA in a high yield rate from fructose, after preparing HMF in the organic solvent having the high boiling point, HMF should be separated from the organic solvent before the oxidizing reaction of HMF.

However, many efforts are needed to separate the organic solvent from HMF, wherein damages of HMF may not be avoided in a separation process.

For example, in the case of removing the solvent by evaporation, a reaction temperature should be maintained at less than 50° C. in order that HMF does not decompose.

Accordingly, in order to remove the solvent having the high boiling point, very low pressure is needed. Therefore, it is nearly impossible to perform the above in a large-scale industrial process, and it is not economical.

As another method, technologies of separating HMF from the organic solvent having the high boiling point by using an organic solvent extractant have been introduced. However, due to limitation of HMF solubility in the organic solvent extractant, there is a problem that efficiency is reduced. Therefore, it is not also economical.

Therefore, in order to economically prepare FDCA from fructose, it is very urgent to develop a method for preparing an intermediate, by which the oxidizing reaction may be directly proceeded without additional post-treatment after dehydration of fructose in the first step.

SUMMARY OF THE INVENTION

The present disclosure is for solving the pre-described problems, and is for providing a method for preparing the intermediate, 5-alkoxymethylfurfural, by which 2,5-furandicarboxylic acid may be prepared in high purity without by-products from fructose.

The problems to be solved by the present disclosure are not limited to the problem(s) noted in the above, and other problem(s) which are not noted may be clearly understood by those skilled in the art from the description below.

In order to solve the above problems, in the preparing method of 5-alkoxymethylfurfural according to one example of the present disclosure, fructose may be added to and react with an organic solvent under an organic acid catalyst, so that 5-alkoxymethylfurfural may be obtained.

Also, the organic acid catalyst may be acetic acid.

Also, the organic solvent may be methanol or ethanol.

The preparing method for 5-alkoxymethylfurfural according to other examples of the present disclosure includes steps of (a) preparing fructose, (b) mixing the fructose, the organic acid catalyst, and the organic solvent, thereby preparing mixing solution, and (c) heating the mixing solution, thereby preparing 5-alkoxymethylfurfural.

Also, the organic solvent may be methanol or ethanol.

Also, the ethanol may be bio-ethanol derived from biomass.

Also, the organic acid catalyst may be acetic acid.

Also, as a concentration of the acetic acid increases, a reaction speed of the step (c) may increase.

Also, the acetic acid may be added in an amount of 1 part by weight to 30 parts by weight with respect to 100 parts by weight of fructose.

Also, in the step (c), pressurization may be atmospheric pressure to 30 bar.

Also, in the step (c), a heating temperature may be 60° C. to 120° C.

According to the present disclosure, 5-alkoxymethylfurfural may be prepared in a high yield rate from fructose that is very plentiful in the vegetable kingdom, so that due to the above, 2,5-furandicarboxylic acid may be prepared without by-products.

Also, by selecting the acetic acid as the organic acid catalyst, 5-alkoxymethylfurfural may be obtained in a high yield rate without generating 5-hydroxymethylfurfural.

Also, by using the organic solvent, 5-alkoxymethylfurfural is formed in solution, so that the oxidizing reaction may be directly proceeded without additional post-treatment such as purification and separation of a catalyst, and 2,5-furandicarboxylic acid may be prepared.

Also, fructose may react with the organic acid catalyst, and the fructose may be converted in a rate of 100%, wherein selectivity of 5-alkoxymethylfurfural of a product increases, and thus 5-alkoxymethylfurfural may be obtained in a very high yield rate.

Also, fructose reacts under eco-friendly organic acid and organic solvent, so that a process load including waste disposal may be reduced.

Effects of the present disclosure are not limited as the above effects. It should be understood that all effects which could be derived from configuration of the invention described in the detailed description of the invention or the scope of claims are included.

DETAILED DESCRIPTION OF TIE EMBODIMENTS

Figure 1:
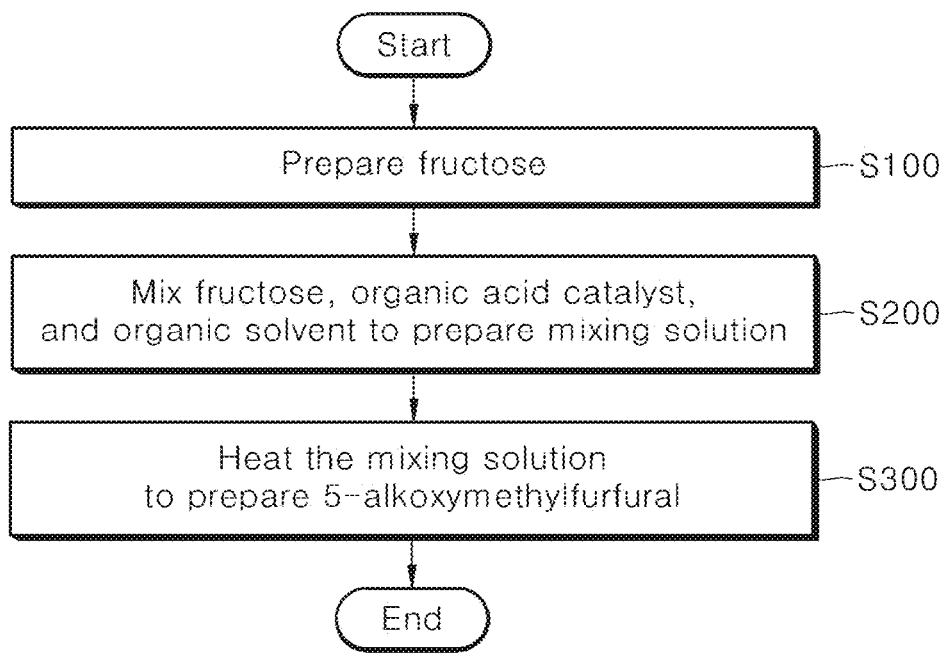
FIG. 1 is a process flow chart which presents a process of a preparing method for 5-alkoxymethylfurfural according to other examples of the present disclosure.

Referring to attached drawings, preferable examples according to the present disclosure will be specifically described hereinafter.

Advantages and features of the present disclosure, and methods to achieve the same will be clarified by referring to examples that will be specifically explained hereafter together with the attached drawings.

However, the present disclosure is not limited by examples disclosed hereinafter but is realized in various different forms. The examples are merely for completing the present disclosure and are provided to completely inform those skilled in the art of categories of the invention. The present disclosure is defined only by the scope of claims.

Also, when the present disclosure is described, if it is deemed that relevant known technologies, etc. could make the gist of the present disclosure vague, the detailed description thereof may be omitted.

When dehydration of fructose is performed in aqueous solution, generated 5-hydroxymethylfurfural (hereinafter, referred to as "HMF") is easily decomposed into levulinic acid and formic acid by a secondary reaction with water. Accordingly, there is a problem such that when 2,5-furandicarboxylic acid (hereinafter, referred to as "FDCA") is prepared, a yield rate thereof is very low. With respect to the above, it was confirmed that if FDCA is prepared by a one-pot reaction using 5-alkoxymethylfurfural (hereinafter, referred to as "AMF") as an intermediate, FDCA may be obtained in a high yield rate without generation of by-products. Therefore, the present inventors have completed a method for preparing AMF by using the organic acid catalyst and the organic solvent from fructose.

According to the present inventors' understanding, a method of preparing AMF by selecting acetic acid as the organic acid catalyst and using ethanol or methanol as the organic solvent in a process of dehydration of fructose has not been disclosed yet.

In the preparing method of 5-alkoxymethylfurfural according to one example of the present disclosure, fructose is added to the organic solvent under the organic acid catalyst, and the above is heated, so that 5-alkoxymethylfurfural (hereinafter, referred to as "AMF") may be obtained.

Since fructose may be easily obtained in biomass including plant resources, and may less generate by-products in a process of dehydration using a solvent compared to glucose, sucrose, or galactose, it is preferable to select the above as a start material for generating AMF.

[Reaction Formula 1]

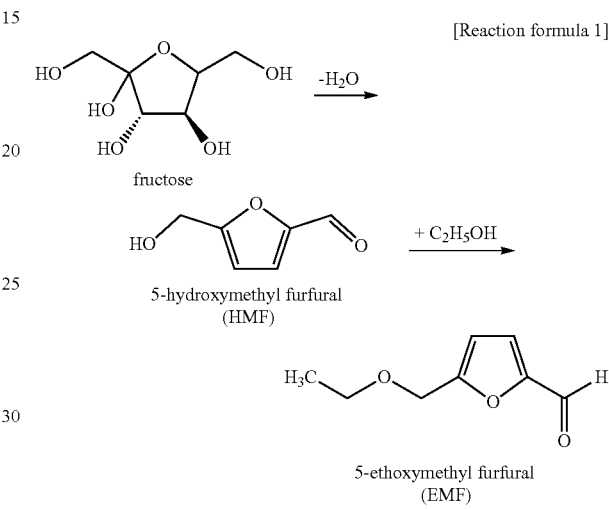

[Reaction formula 1]

Reaction formula 1 presents reaction steps in the preparing method of 5-ethoxymethylfurfural according to one example of the present disclosure.

Fructose as the start material is mixed with ethanol, and the same is heated, so that 5-ethoxymethylfurfural (hereinafter, referred to as "EMF") may be obtained.

Here, acetic acid may be added as the organic acid catalyst.

When the acetic acid is used as the organic acid catalyst, a generation speed of EMF may increase, and thus a yield rate of recovered EMF may effectively increase.

The organic solvent may be methanol or ethanol.

Hereinafter, it is meant that AMF includes 5-methoxymethylfurfural obtained by methanol as the organic solvent and 5-ethoxymethylfurfural obtained by ethanol as the organic solvent.

By using the organic solvent and acetic acid, AMF may be effectively prepared without by-products in dehydration.

FIG. 1 is a process flow chart which presents a process of the preparing method for 5-alkoxymethylfurfural according to other examples of the present disclosure.

Referring to FIG. 1, the preparing method for 5-alkoxymethylfurfural according to other examples of the present disclosure includes steps of (a) preparing fructose, (b) mixing the fructose, the organic acid catalyst, and the organic solvent, thereby preparing mixing solution, and (c) heating the mixing solution, thereby preparing 5-alkoxymethylfurfural.

In advance, fructose is prepared (S100).

The fructose may be obtained from biomass in a way such that butanol as a solvent reacts under solid acid or base catalysts.

When fructose is obtained by butanol as the solvent, the fructose may be obtained in a high yield rate.

When the others except the fructose among monosaccharides derived from biomass are heated by the organic acid catalyst, there is a problem that a yield rate of AMF is not high.

Mixing solution is prepared by mixing the fructose, the organic acid catalyst, and the organic solvent (S200).

By mixing the organic acid catalyst and the organic solvent, preparing mixing solution, and heating the same, 5-alkoxymethylfurfural may be formed in solution.

By using solution including formed 5-alkoxymethylfurfural, the oxidizing reaction is directly proceeded without additional post-treatment such as purification and separation of the catalyst. Accordingly, 2,5-furandicarboxylic acid may be prepared by a subsequent continuous process.

The organic acid catalyst is acetic acid.

When the acetic acid is used as the organic acid catalyst, a generation speed of EMF may increase, and thus a yield rate of recovered EMF may effectively increase.

The organic solvent may be methanol or ethanol.

When methanol or ethanol is selected as the organic solvent, MMF or EMF may be obtained in a very high yield rate without generation of by-products.

The ethanol may be bio-ethanol derived from biomass.

The case that ethanol is bio-ethanol, and the organic acid catalyst is acetic acid is eco-friendly, wherein a load for treating by-products may be greatly reduced compared to an inorganic acid catalyst.

Meanwhile, as a concentration of the acetic acid increases, a reaction speed of S300 may increase.

By controlling the concentration of the acetic acid, the generation speed of 5-alkoxymethylfurfural may be controlled.

The acetic acid may be added in an amount of 1 part by weight to 30 parts by weight with respect to 100 parts by weight of fructose.

If an added amount of the acetic acid is less than the above range, there is a problem that AMF may not be sufficiently generated. If the amount exceeds the above range, there is a problem that selectivity of recovered AMF is lowered.

By heating the mixing solution, 5-alkoxymethylfurfural is prepared (S300).

The mixing solution may be pressurized by atmospheric pressure or 30 bar.

When a pressure range is less than the above range, a yield rate of recovered AMF is lowered. When it exceeds the above range, energies are excessively consumed, and thus the yield rate of AMF is not heightened.

The mixing solution may be heated in a temperature of 60° C. to 120° C.

By reacting in the above temperature range, AMF may be generated and recovered.

When the temperature range is less than the above range, the yield rate of recovered AMF is very lowered. When it exceeds the above range, energies are excessively consumed, and thus the yield rate of AMF is not heightened compared to an amount of energy consumption.

AMF obtained by other examples of the present disclosure may be used as the intermediate for preparing FDCA.

Hereinafter, preferable examples are presented for assisting understanding of the present disclosure. However, examples below are merely for exemplifying the present disclosure, wherein the scope of the present disclosure is not limited by examples below.

Experimental Example 1: Comparison of Chemical Stability

Figure 2:
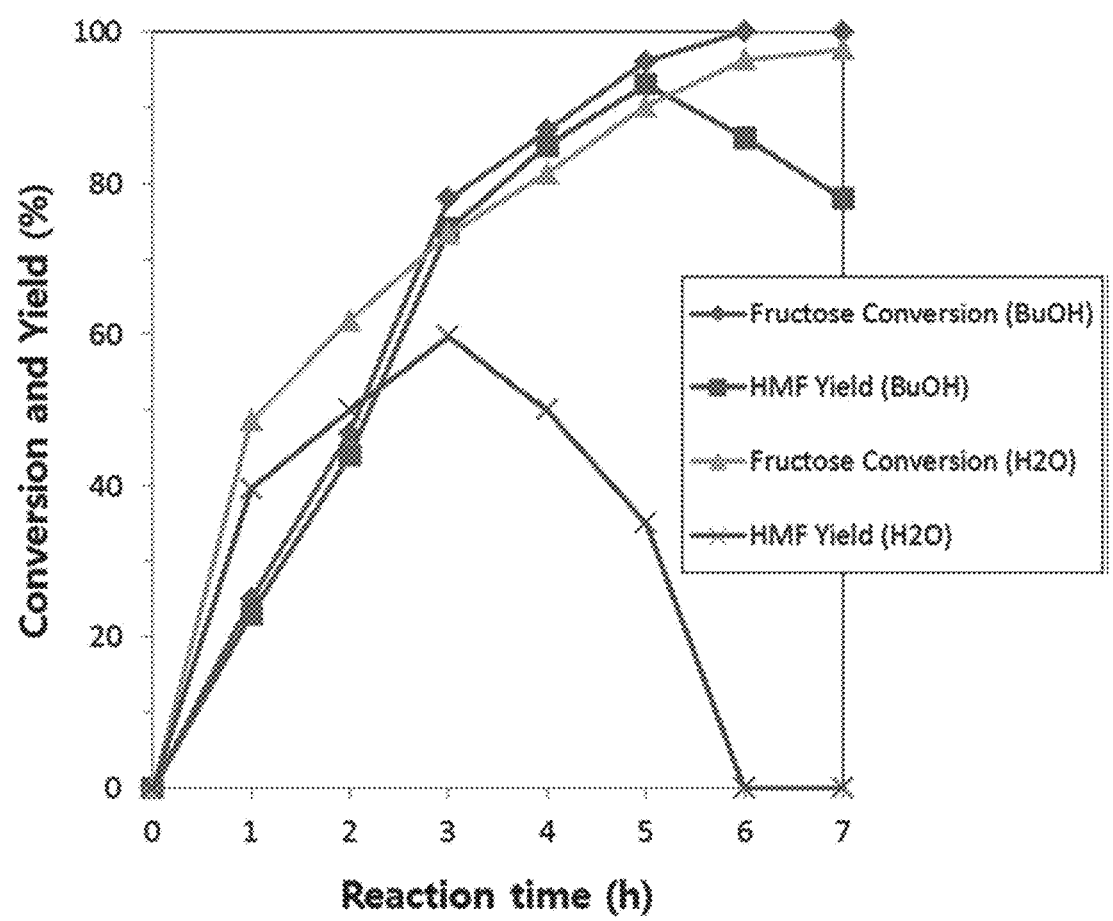
FIG. 2 is a graph which presents a conversion rate of fructose and a yield rate of HMF according to solvents.

FIG. 2 is a graph which presents a conversion rate of fructose and a yield rate according to solvents.

After mixing 1.0 g of a catalyst, Amberlyst-15, 15 g of fructose, and 85 g of a solvent and reacting at 100° C., a conversion rate and a yield rate of HMF were checked.

Referring to FIG. 2, it was exhibited that a conversion rate of fructose in a butanol solvent is higher than a conversion rate thereof in aqueous solution. Meanwhile, it was confirmed that HMF is chemically unstable depending on reaction time, so that due to levulinic acid and formic acid generated by hydrolysis and human generated by condensation, the yield rate thereof is very lowered.

TABLE 1

| Sample | Temp. (° C.) | Time (h) | Initial composition (wt. %) | Final composition (wt. %) |
|---|---|---|---|---|
| MMF in Methanol | 30 | 48 | 8.98 | 8.97 |
|  | 50 | 24 | 8.97 | 8.95 |
|  | 60 | 24 | 8.95 | 8.94 |
|  | 60 | 48 | 8.94 | 8.93 |
| EMF in Ethanol | 30 | 48 | 9.88 | 9.88 |
|  | 50 | 24 | 9.88 | 9.97 |
|  | 60 | 24 | 9.97 | 9.97 |
|  | 60 | 48 | 9.97 | 9.96 |

Table 1 presents changes of a composition according to a reaction temperature and time of MMF and EMF.

Referring to Table 1, it was confirmed that in the case of MMF and EMF, there are nearly no changes of initial and final compositions depending on changes of a temperature and time. Further, it was confirmed that MMF and EMF are chemically stable even in a catalyst reaction condition.

Therefore, it was confirmed that MMF and EMF are preferable as the intermediate for preparing FDCA.

Example 1

After mixing 1 g of fructose with 9 ml of ethanol and 0.05 g of acetic acid as an organic acid catalyst, and heating the same at 70° C. in atmospheric pressure, a reaction was proceeded for 20 hours. After the reaction, as a result of analyzing solution by liquid chromatography, it was confirmed that a conversion rate of fructose is 100%, and a yield rate of EMF is 90%.

Example 2: Confirmation of Yield Rate According to Pressurization

After mixing 1 g of fructose with 9 ml of ethanol and 0.05 g of acetic acid as an organic acid catalyst, pressurizing the same by 25 bar, and heating the same at 100° C., a reaction was proceeded for 8 hours. After the reaction, as a result of analyzing solution by liquid chromatography, it was confirmed that a conversion rate of fructose is 100%, and a yield rate of EMF is 92%.

Example 3: Confirmation of Yield Rate According to Amount of Acetic Acid as Catalyst After mixing 1 g of fructose with 9 ml of ethanol and 0.1 g of acetic acid as an organic acid catalyst, and heating the same at 70° C. in atmospheric pressure, a reaction was proceeded for 12 hours. After the reaction, as a result of analyzing solution by liquid chromatography, it was confirmed that a conversion rate of fructose is 100%, and a yield rate of EMF is 87%.

Example 4: Confirmation of Yield Rate According to Amount of Acetic Acid as Catalyst After mixing 1 g of fructose with 9 ml of ethanol and 0.2 g of acetic acid as an organic acid catalyst, and heating the same at 70° C. in atmospheric pressure, a reaction was proceeded for 6 hours. After the reaction, as a result of analyzing separated solution by liquid chromatography, it was confirmed that a conversion rate of fructose is 100%, and a yield rate of EMF is 84%.

Example 5: Confirmation of Yield Rate According to Amount of Acetic Acid as Catalyst After mixing 1 g of fructose with 9 ml of ethanol and 0.3 g of acetic acid as an organic acid catalyst, and heating the same at 70° C. in atmospheric pressure, a reaction was proceeded for 4 hours. After the reaction, as a result of analyzing separated solution by liquid chromatography, it was confirmed that a conversion rate of fructose is 100%, and a yield rate of EMF is 82%.

Example 6: Confirmation of Yield Rate According to Pressurization

After mixing 1 g of fructose with 9 ml of ethanol and 0.05 g of acetic acid as an organic acid catalyst, pressurizing the same by 15 bar, and heating the same at 100° C., a reaction was proceeded for 10 hours. After the reaction, as a result of analyzing separated solution by liquid chromatography, it was confirmed that a conversion rate of fructose is 100%, and a yield rate of EMF is 80%.

Comparative Example 1: Preparation of EMF Using Inorganic Catalyst

After mixing 1 g of fructose with 9 ml of ethanol and 0.03 g of sulfuric acid ($H_2SO_4$) as an inorganic acid catalyst, and heating the same at 90° C. in 25 bar, a reaction was proceeded for 6 hours. After the reaction, as a result of analyzing solution by liquid chromatography, it was confirmed that a conversion rate of fructose is 85%, and a yield rate of EMF is 32%.

Comparative Example 2: Preparation of EMF Using Industrial Solid Acid as Catalyst After mixing 1 g of fructose with 9 ml of ethanol and 0.25 g of Amberlyst-15, and heating the same at 90° C. in 25 bar, a reaction was proceeded for 6 hours. After the reaction, a solid acid catalyst is separated from solution. As a result of analyzing solution by liquid chromatography, it was confirmed that a conversion rate of fructose is 92%, and a yield rate of EMF is 44%.

Comparative Example 3: Confirmation of Yield Rate According to Amount of Acetic Acid as Catalyst After mixing 1 g of fructose with 9 ml of ethanol and 0.1 g of acetic acid as an organic acid catalyst, and heating the same at 70° C. in atmospheric pressure, a reaction was proceeded for 2 hours. After the reaction, as a result of analyzing solution by liquid chromatography, it was confirmed that a conversion rate of fructose is 100%, and a yield rate of EMF is 41%.

Example 7: Preparation of FDCA from EMF Derived from Fructose

After mixing 10 ml of EMF/ethanol mixing solution prepared by example 1 with 0.5 g of a Pt(5%)/C catalyst, and pressurizing an oxygen gas thereinto by 15 bar, a reaction was proceeded for 2 hours at 100° C.

After the reaction, the above was cooled to a room temperature, and a solid mixture was separated from a filtrate by filtration. As a result of analyzing the filtrate by liquid chromatography, it was confirmed that a conversion rate of EMF is 100%.

After mixing the solid mixture with 10 ml of dimethylformamide (DMF) as a solvent, the catalyst was separated from solution by filtration. As a result of analyzing separated solution by liquid chromatography, it was confirmed that a yield rate of FDCA is 90%.

Referring to the examples and the comparative examples, the following was confirmed. In the case that EMF is prepared by mixing fructose with an ethanol solvent by using acetic acid as the organic acid catalyst, and heating the above, not only EMF may be obtained in a high yield rate of 80% or more, but also HMF is not generated, and generation of by-products may be effectively prevented compared to the case of using the inorganic acid or solid acid as the catalyst, within a specific concentration and temperature range.

Also, according to example 7, it was newly confirmed that by an EMF intermediate prepared by the present disclosure, FDCA may be prepared in a high yield rate directly through the oxidizing reaction without an additional catalyst separation process.

As the above, specific examples related to the preparing method of 5-alkoxymethylfurfural according to the examples of the present disclosure were explained. However, it is obvious that various modifications are possible within the scope of the present disclosure.

Therefore, the scope of the present disclosure should not be defined to be limited as the explained examples. Rather, the scope of the present disclosure should be defined by the scope of claims to be described hereafter and equivalents thereof.

That is, the above-described examples are exemplary in all aspects and are not be interpreted as limiting the present disclosure. Additionally, the scope of the disclosure is defined according to the appended claims rather than the detailed description. Further, all the modifications and modified forms drawn from the meanings and scopes of the claims and the equivalents thereof should be interpreted as being included in the scope of the present disclosure.

What is claimed is:

1. A preparing method for 5-alkoxymethylfurfural, wherein fructose is added to and reacts with an organic solvent under an organic acid catalyst, thereby obtaining 5-alkoxymethylfurfural,
    wherein the organic acid catalyst is acetic acid,
    wherein the acetic acid is added in an amount of 1 part by weight to 30 parts by weight with respect to 100 parts by weight of fructose.

2. The preparing method for 5-alkoxymethylfurfural of claim 1, wherein the organic solvent is methanol or ethanol.

3. A preparing method for 5-alkoxymethylfurfural, comprising steps of:

(a) preparing fructose;
(b) mixing the fructose, an organic acid catalyst, and an organic solvent, thereby preparing mixing solution; and
(c) heating the mixing solution, thereby preparing 5-alkoxymethylfurfural,
wherein the organic acid catalyst is acetic acid,
wherein the acetic acid is added in an amount of 1 part by weight to 30 carts by weight with respect to 100 parts by weight of fructose.

4. The preparing method for 5-alkoxymethylfurfural of claim 3, wherein the organic solvent is methanol or ethanol.

5. The preparing method for 5-alkoxymethylfurfural of claim 3, wherein in the step (c), pressurization is atmospheric pressure to 30 bar.

6. The preparing method for 5-alkoxymethylfurfural of claim 3, wherein in the step (c), a heating temperature is 60° C. to 120° C.

7. A method of preparing 2,5-furandicarboxylic acid comprising first preparing 5-alkoxymethylfurfural, wherein fructose is added to and reacts with an organic solvent under an organic acid catalyst wherein the organic acid catalyst is acetic acid, wherein the acetic acid is added in an amount of 1 part by weight to 30 parts by weight with respect to 100 parts by weight of fructose thereby obtaining 5-alkoxymethylfurfural, followed by using the 5-alkoxymethylfurfural to prepare 2,5-furandicarboxylic acid.

* * * * *